United States Patent [19]
Lovrecich

[11] Patent Number: 5,354,560
[45] Date of Patent: Oct. 11, 1994

[54] SUPPORTED DRUGS WITH INCREASED DISSOLUTION RATE, AND A PROCESS FOR THEIR PREPARATION

[75] Inventor: Mara L. Lovrecich, Trieste, Italy

[73] Assignee: Vectorpharma International, S.p.A., Trieste, Italy

[21] Appl. No.: 827,496

[22] Filed: Jan. 30, 1992

Related U.S. Application Data

[63] Continuation of Ser. No. 441,969, Nov. 28, 1989, abandoned.

[30] Foreign Application Priority Data

Nov. 28, 1989 [IT] Italy ................ 22770 A/88

[51] Int. Cl.$^5$ ................................. A61K 9/14
[52] U.S. Cl. .................... 424/489; 424/499; 424/500; 424/501; 241/18
[58] Field of Search ............ 424/489, 499, 500, 501, 424/78.08; 241/18

[56] References Cited

U.S. PATENT DOCUMENTS

| | | | |
|---|---|---|---|
| 3,328,256 | 6/1967 | Gaunt | 424/501 |
| 3,499,784 | 3/1970 | Bentholm | 241/18 |
| 3,966,899 | 6/1976 | Nakai | 424/468 |
| 4,111,371 | 9/1978 | Melliger | 241/18 |
| 4,639,370 | 1/1987 | Carli | 424/80 |
| 4,837,031 | 6/1989 | Denton | 424/464 |

FOREIGN PATENT DOCUMENTS 0129893  2/1985  European Pat. Off. .

*Primary Examiner*—G. S. Kishore
*Attorney, Agent, or Firm*—Birch, Stewart, Kolasch & Birch

[57] ABSTRACT

Supported drugs with an increased dissolution rate, prepared by a process comprising mixing the drug with the support material under dry conditions, co-grinding the mixture in a mill with its grinding chamber saturated with the vapour of one or more solvents able to solubilize the drug or to be adsorbed on the surface of the support material, vacuum-drying the product obtained, and sieving. The drugs obtained in this manner have a reduced heat of fusion, a reduced melting point, an increased dissolution rate and an increased solubilization kinetics.

14 Claims, No Drawings

SUPPORTED DRUGS WITH INCREASED DISSOLUTION RATE, AND A PROCESS FOR THEIR PREPARATION

This application is a continuation of application Ser. No. 07/441,969 filed on Nov. 28, 1989, now abandoned, the entire contents of which are incorporated herein by reference.

FIELD OF THE INVENTION

This invention relates to supported drugs possessing characteristics which result in an increase in their rate of dissolution.

PRIOR ART

It has for some time been widespread practice in the pharmaceutical field to grind or micronize poorly soluble drugs with a view to improving their biopharmaceutical properties by virtue of the resultant increase in surface area.

In addition to this general method, there has in recent years been an ongoing development in the technique of high-energy grinding, applied to mixtures comprising the drug and special support materials. This technique is based on two basic elements:

1) the use of mills (of single or multi-ball type, mortar type, etc.) in which the impact or friction energy between the grinding means and the powder is particularly high;

2) the use of support materials which facilitate the desired physicochemical transformations of the drug.

The primary objective of this grinding technique is the total or partial eunorphization of the drug originally in the crystalline state. Amorphization results in drug solubilization kinetics having a profile involving supersaturation concentrations which are much higher than those obtainable with the drug in its crystalline state.

A further objective of this grinding technique is to improve the wettability characteristics and dissolution rate of the drug. In the U.S. Pat. Nos. 3,966,899 and 4,036,990, high-energy grinding of mixtures of drugs and $\beta$-1,4-glucan is used to increase the dissolution rate of poorly soluble drugs; the product amorphization is followed by X-ray diffractometry.

In Japanese Patent 7986607 the support material used in the co-grinding is $\beta$-cyclodextrin, used either alone or together with other excipients such as lactose, calcium phosphate and starch, which are already present during the grinding.

$\beta$-cyclodextrin is also used in the DE Patent 3427788 to obtain inclusion complexes of benzimidazole derivatives by grinding with a ball mill. The use of microcrystalline cellulose in high-energy co-grinding is described in Chem. Pharm. Bull., 78, 3340-6, 1977; Chem. Pharm. Bull., 78, 3419-25, 1978 and Chem. Pharm. Bull., 28, 652-6, 1980; thermal analysis and IR spectrophotometry are applied in studying the support/drug interactions.

In the EP Patent 129893 silica gel or other adsorbent materials are used in the high-energy co-grinding of drugs such as griseofulvin, chloramphenicol and theophylline either to obtain improved dissolution rates or for amorphization.

The U.S. Pat. No. 4,639,370 describes the use of co-grinding of polymers which are swellable but insoluble in water such as cross-linked polyvinylpyrrolidone, cross-linked sodium carboxymethylcellulose and dextran; the low-solubility drugs studied include medroxyprogesterone acetate, griseofulvin and indomethacin.

In all the preceding patents regarding high-energy co-grinding of drug-support mixtures, the procedure used is essentially to premix the components and then co-grind them under dry conditions for the time required to obtain the desired amorphization and/or dissolution rate characteristics. In some cases the necessary grinding time can be particularly long, reaching and sometimes exceeding 24 hours.

SUMMARY OF THE INVENTION

We have now discovered a process for preparing supported drugs based on co-grinding the active substance with a support material, which has considerable advantages over the processes of the known art.

With the process according to the invention, for equal co-grinding times, the drug dissolution rate is decidedly higher, with pharmacokinetic advantages. In addition, a shorter co-grinding time is sufficient to obtain the same drug dissolution rate, thus resulting in cost advantages and the possibility of processing low-stability drugs which could degrade under prolonged co-grinding times. Said process is characterised in that:

a) the active substance and support material, in the form of powders, are mixed and possibly degassed;

b) the mixture is co-ground is a mill in which the grinding chamber is saturated with the vapour of one or more solvents able to solubilize the active substance or to be adsorbed on the surface of the support material;

c) on termination of the co-grinding the product is dried under vacuum and sieved to eliminate any aggregates.

The products obtained by the process according to the present invention are characterised by a reduction in the residual crystallinity of the active substance indicated by a reduction in the heat of fusion, a reduction in the crystal dimensions to nanometer level indicated by a reduction in the melting point, an increase in the dissolution rate and an increase in the solubilization kinetics.

DETAILED DESCRIPTION OF THE INVENTION

The characteristics and advantages of the supported drugs and of their preparation process according to the present invention will be more apparent from the following detailed description. The active substance and the support material, both in powder form, are mixed together in a solids mixed. The active substance has a particle size distribution of between 0.01 and 1000 microns and preferably between 0.01 and 100 microns, and the support material has a particle size distribution of between 0.01 and 1000 microns and preferably between 1 and 100 microns.

The mixture can be heated under vacuum to a temperature compatible with the stability of the constituent substances to de-adsorb any foreign substances which may be present.

Said heating can be done in the same chamber as that in which the co-grinding is to be carried out.

The mixture obtained in this manner is introduced into the grinding chamber together with the grinding means. The chamber is connected by a valve to a storage vessel containing the relevant solvent in the gaseous state.

Grinding is commenced and the valve simultaneously opened so that the gaseous-phase solvent can enter the grinding chamber. Alternatively, the grinding chamber can be pressurized with the gaseous-phase solvent by opening the connection valve immediately after introducing the mixture, the actual grinding being commenced only after a time period sufficient for the chamber to be saturated. The co-grinding is conducted for a time of between 0.10 and 48 hours, and preferably between 0.25 and 4 hours. The product obtained has a particle size distribution of between 0.01 and 100 microns.

On termination of the co-grinding operation, the mixture is placed in an oven under vacuum, or another similar apparatus, and dried at a temperature compatible with the stability of the mixture substances. After drying, the product is sieved to eliminate any formed aggregates. The mill for the process according to the invention is of the type based on high impact energy between the grinding means and the powder. Non-limiting examples of such mills are rotary mills, high vibration mills, ball mills, roller mills, mortar mills, planetary mills, etc. Many drugs are suitable for preparation by the process of the present invention, such as anti-inflammatories, analgesics, tranquilizers, sedatives, oral antitumorals etc. Drugs which are particularly suitable for preparation by the process of the present invention are griseofulvin, piroxicam, diacerein, diltiazem, megestrol acetate, nifedipine, nicergoline and the like, ketoprofen, naproxen, diclofenac, ibuprofen, lorazepam, oxazepam etc.

The solvents are chosen from those which can be adsorbed by the support material and those able to act as solvents for the active substance. By way of example, solvents suitable for use in the present invention are water, methylene chloride, chloroform, methanol, ethanol, isopropanol and their mixtures.

The support materials usable in the co-grinding for the purposes of the invention are:

cross-linked polymers swellable in water, such as crospovidone, cross-linked polymeric cyclodextrin, cross-linked sodium carboxymethyl starch, dextran etc.;

water-soluble complexing agents, such as cyclodextrin and derivatives;

high area and/or porosity inorganic materials such as silica gel, titanium dioxide, aluminium oxides etc.;

hydrophilic linear polymers such as polyvinyl-pyrrolidone, cellulose or derivatives etc. The weight ratio of support material to drug is between 100:1 and 1:10 and preferably between 10:1 and 1:1. The characteristics of the products obtainable by the high-energy co-grinding technique of this invention can be defined by various methods, such as:

determination of dissolution rate;
determination of solubilization kinetics;
differential scanning calorimetry to measure the heat of fusion, which is related to the residual crystallinity of the drug;
differential scanning calorimetry of other thermoanalytical method to evaluate the reduction in melting point, which is related to the reduction of the dimensions of the drug crystals to nanometer levels.

The process according to the present invention has important advantages over the known art.

Firstly, a shorter co-grinding time is sufficient to attain the required degree of crystalline destructuring of the drug, with consequent considerable advantages in energy costs. In addition, a shorter co-grinding time can allow processing of low-stability drugs which could degrade under prolonged co-grinding times. For equal co-grinding times the products obtained by the method of the invention, when compared with those obtained by the prior art, have the following advantages, existing either simultaneously or individually:

higher degree of amorphization (lesser residual crystallinity of the drug);

greater reduction in the dimensions of the drug crystalline residues, as far as nanometer levels, as shown by the greater lowering in the drug melting point;

in the case of cross-linked polymeric or porous inorganic support materials there is a greater drug concentration in the surface layers of the support material;

the dissolution rate and/or the solubilization kinetics are decidedly higher.

The supported drugs according to the present invention can be used in the preparation of various pharmaceutical forms such as tablets and capsules (of immediate or controlled release), suspensions, transdermic films etc.

For preparing immediate-release tablets or capsules they can be mixed with excipients normally used in the pharmaceutical field such as lactose, starch, calcium phosphate, microcrystalline cellulose etc. To prepare controlled-release tablets or capsules, said supported drugs can be mixed with polymers such as methylcellulose and derivatives, polymethylmethacrylates, ethylcellulose etc.

The following examples of the preparation of supported drugs according to the present invention are given for purposes of non-limiting illustration. The characterisation of the products obtained is given at the end of the examples.

EXAMPLE 1

4 g of griseofulvin and 8 g of crospovidone (Kollidon-CL, BASF) are sieved through a 60 mesh sieve and mixed together for 10 minutes. The mixture is placed in the grinding chamber of a high-energy colloidal mill together with the grinding means. The valve connecting the mill to a vessel containing methylene chloride is opened and the grinding chamber allowed to become saturated with methylene chloride vapour. Co-grinding is then carried out for 2 hours while maintaining saturation conditions. On termination of co-grinding, the resultant powder has a particle size of between 1 and 100 microns. It is dried at 30° C. under vacuum for 3 hours and then sieved through a 60 mesh sieve.

EXAMPLE 2

4 g of griseofulvin and 4 g of crospovidone are sieved through a 60 mesh sieve and mixed together for 10 minutes. The mixture is placed in the grinding chamber of a high-energy colloidal mill together with the grinding means. The grinding chamber is saturated with vapour from methylene chloride contained in a vessel connected to the mill via a valve. Co-grinding is then carried out for 2 hours while maintaining saturation conditions.

On termination of co-grinding, the resultant powder has a particle size of between 1 and 100 microns.

It is dried at 30° C. under vacuum for 3 hours and then sieved through a 60 mesh sieve and mixed.

EXAMPLE 3

2.5 g of diacerein and 7.5 g of crospovidone are sieved through a 60 mesh sieve and placed in the grinding chamber of a high-energy colloidal mill. The mill is operated for a few seconds to mix the powders together with the grinding means. The valve connecting the mill to a vessel containing methylene chloride is opened and the grinding chamber allowed to become saturated with the solvent vapour. Cogrinding is then carried out for 1 hour under saturation conditions. The resultant powder has a particle size of between 1 and 100 microns. It is dried at 30° C. under vacuum for 3 hours, sieved through a 60 mesh sieve and then mixed.

EXAMPLE 4

5 g of megestrol acetate and 10 g of crospovidone are sieved through a 60 mesh sieve, mixed together and placed in the grinding chamber of a high-energy colloidal mill together with the grinding means. The chamber is then saturated with methylene chloride vapour by opening the valve connecting the mill to the vessel containing methylene chloride, and co-grinding is then carried out for 4 hours. On termination, the resultant powder has a particle size of between 1 and 100 microns. It is dried at 50° C. under vacuum for 3 hours, sieved through a 60 mesh sieve and then mixed.

EXAMPLE 5

3.5 g of megestrol acetate and 10.5 g of micronized crospovidone are sieved through a 60 mesh sieve, mixed together and placed in the grinding chamber of a high-energy colloidal mill together with the grinding means. The powder is heated to 80° C. for 2 hours under vacuum. The chamber is saturated with methylene chloride vapour generated by a vessel connected to the mill via a valve, and co-grinding is then carried out for 2 hours. On termination, the resultant powder has a particle size of between 0.1 and 50 microns. It is dried at 30° C. under vacuum for 5 hours, sieved through a 60 mesh sieve and then mixed.

EXAMPLE 6

4 g of piroxicam and 12 g of micronized crospovidone are sieved through a 60 mesh sieve, mixed together and placed in the grinding chamber of a high-energy colloidal mill together with the grinding means. The chamber is saturated with methylene chloride vapour generated by a vessel connected to the mill via a valve, and co-grinding is then carried out for 2 hours. On termination, the resultant powder has a particle size of between 0.1 and DO microns. It is dried at 30° C. for 3 hours under vacuum, sieved through a 60 mesh sieve and then mixed.

EXAMPLE 7

4 g of megestrol acetate and 12 g of beta-cyclodextrin (CHINOIN) are sieved separately through a 60 mesh sieve, mixed together and placed in the grinding chamber of a high-energy colloidal mill. The chamber is saturated with methylene chloride vapour generated by a vessel connected to the mill via a valve, and co-grinding is then carried out for 2 hours. On termination, the resultant powder has a particle size of between 0.1 and 100 microns. It is dried at 30° C. for 3 hours under vacuum, sieved through a 60 mesh sieve and then mixed.

EXAMPLE 8

1 g of piroxicam and 9.16 g of beta-cyclodextrin are sieved separately through a 60 mesh sieve, mixed together and placed in the grinding chamber of a high-energy colloidal mill together with the grinding means. The chamber is saturated with methylene chloride vapour originating from a vessel connected to the mill via a valve, and co-grinding is then carried out for 1 hour. On termination, the resultant powder has a particle size of between 0.1 and 100 microns. It is dried, sieved through a 60 mesh sieve and then mixed.

EXAMPLE 9

1 g of piroxicam and 3.05 of beta-cyclodextrin are sieved separately through a 60 mesh sieve, mixed together and placed in the grinding chamber of a high-energy colloidal mill together with the grinding means. The powder is heated to 80° C. for 1 hour under vacuum. The chamber is then saturated with methylene chloride vapour originating from a vessel connected to the mill via a valve, and co-grinding is carried out for 1 hour. On termination, the resultant powder has a particle size of between 0.1 and 100 microns. It is dried, sieved through a 60 mesh sieve and then mixed.

EXAMPLE 10

3 g of diltiazem and 9 g of polymeric beta-cyclodextrin (cross-linked with epichlorohydrin, CHINOIN) are sieved through a 60 mesh sieve, mixed together and placed in the grinding chamber of a high-energy colloidal mill. The chamber is then saturated with water vapour originating from a vessel connected to the mill via a valve, and co-grinding is carried out for 1 hour. The resultant powder has a particle size of between 1 and 100 microns. It is dried at 60° C. for 6 hours under vacuum, sieved through a 60 mesh sieve and then mixed.

EXAMPLE 11

3 g of griseofulvin and 9 g of polymeric beta-cyclodextrin (cross-linked with epichlorohydrin, CHINOIN) are sieved through a 60 mesh sieve, mixed together and placed in the grinding chamber of a high-energy colloidal mill. It is heated to 100° C. for 2 hours under vacuum, the chamber is then saturated with methylene chloride vapour originating from a vessel connected to the mill via a valve, and co-grinding carried out for 2 hours. The resultant product has a particle size of between 1 and 100 microns. It is dried, sieved through a 60 mesh sieve and then mixed.

EXAMPLE 12

4 g of piroxicam and 12 g of silica (Si-60, MERCK) are sieved through a 60 mesh sieve, mixed together and placed in the grinding chamber of a high-energy colloidal mill together with the grinding means. The chamber is saturated for 24 hours with methylene chloride vapour originating from a vessel connected to the mill via a valve, and co-grinding is then carried out for 2 hours. The resultant product has a particle size of between 0.1 and 50 microns. It is dried, sieved through a 60 mesh sieve and then mixed.

EXAMPLE 13

3 g of nicergoline and 9 g of crospovidone are sieved through a 60 mesh sieve and mixed for 10 minutes. The mixture is placed in the grinding chamber of a high-energy colloidal mill together with the grinding means. The grinding chamber is saturated with vapour from methylene chloride contained in a vessel connected to the mill via a valve. Cogrinding is then carried out for 3 hours while maintaining saturation conditions. The resultant powder has a particle size of between 1 and 100 microns. It is dried at 30° C. under vacuum for 3 hours, sieved through a 60 mesh sieve and mixed. The following examples of the preparation of supported drugs of the known art are provided to enable useful comparison with the preceding examples to be made. The characterisation of the obtained products is described at the end of the examples.

EXAMPLE A 4 g of griseofulvin and 8 g of crospovidone are co-ground exactly as described in Example 1, but without saturating the mill chamber with methylene chloride vapour.

EXAMPLE B 4 g of griseofulvin and 4 g of crospovidone are co-ground as described in Example 2, but without saturating the mill chamber with methylene chloride vapour.

EXAMPLE C 2.5 g of diacerein and 7.5 g of crospovidone are co-ground as described in Example 3, but without saturating the mill chamber with methylene chloride vapour.

EXAMPLE D 5 g of megestrol acetate and 10 g of crospovidone are co-ground as described in Example 4, but without saturating the mill chamber with methylene chloride vapour.

EXAMPLE E 3.5 g of megestrol acetate and 10.5 g of crospovidone are co-ground as described in Example D, but without preheating the powder to 80° C. and without saturating the mill chamber with methylene chloride vapour.

EXAMPLE F 4 g of piroxicam and 12 g of micronized crospovidone are co-ground as described in Example 6, but without saturating the mill chamber with methylene chloride vapour.

EXAMPLE G 4 g of megestrol acetate and 12 g of beta-cyclodextrin are co-ground exactly as in Example 7, but without saturating the mill chamber with methylene chloride vapour.

EXAMPLE H 1 g of piroxicam and 9.16 g of beta-cyclodextrin are co-ground as described in Example 8, but without saturating the mill chamber with methylene chloride vapour.

EXAMPLE I 1 g of piroxicam and 3.05 g of beta-cyclodextrin are co-ground as described in Example 9, but without preheating the mixture of the two powders to 80° C. and without saturating the mill chamber with methylene chloride vapour.

EXAMPLE L 3 g of diltiazem and 9 g of cross-linked polymeric beta-cyclodextrin are co-ground as in Example 10, but without saturating the mill chamber with water vapour.

EXAMPLE M 3 g of griseofulvin and 9 g of polymeric beta-cyclodextrin (cross-linked with epichlorohydrin, CHINOIN) are co-ground as in Example 11, but without saturating the mill chamber with methylene chloride vapour.

EXAMPLE N 4 g of piroxicam and 12 g of silica SI-60 are co-ground as in Example 12, but without saturating the mill chamber with methylene chloride vapour.

CHARACTERISATION TESTS

The results are given below of characterisation tests carried out on products obtained by the process of the invention, compared with similar products obtained by the known art. The characterisation was effected by:
determining the dissolution rate
determining the solubilization kinetics;
differential scanning calorimetry.

Determination of dissolution rate

The dissolution rate data for the supported drugs prepared by the process of this invention (Examples 1-12) are shown in Tables 1 to 9, in comparison with the dissolution rate data for the supported drugs prepared by known processes (Examples A to N).

For all the studied drugs the method used was that of USP XX No. 2, utilising a SOTAX apparatus at 37° C. and a Beckman DU 65 spectrophotometer. In all cases the sample quantities used are such as to ensure that sink conditions (i.e. concentrations of 20% less than solubility) are maintained.

For products containing griseofulvin, 900 ml of a pH 7.5 buffer solution stirred at 150 r.p.m. were used; the spectrophotometric reading of suitably diluted samples was taken at 294 nm.

For products containing diacerein, 900 ml of pH 5.5 buffer solution stirred at 100 r.p.m. were used; the spectrophotometric reading was taken at 255 nm.

For products containing megestrol acetate, 900 ml of a pH 5.2 phosphate buffer solution stirred at 150 r.p.m. were used; the concentrations were determined by HPLC using a SPECTRA PHYSICS Mod. SP 4290/SP 8800 apparatus, mobile phase acetonitrile/$H_2O$ 50/50 v/v with flow rate 1 ml/min, column NOVAPAK $C_{18}$, detector VV Mod. SP 8490, at 292 nm. For products containing piroxicam, 900 ml of a pH 5.0 buffer solution stiffed at 100 r.p.m. were used; the spectrophotometric reading was taken at 356 nm.

As can be seen from the data given in Tables 1-9, for all drugs and all support materials used the dissolution rate was higher for products prepared by the process of this invention than for similar products prepared by the known art.

TABLE 1

| Dissolution rate of products consisting of griseofulvin/crospovidone 1:2 weight/weight | | |
|---|---|---|
| | Griseofulvin concentration ($\mu$g/ml) | |
| Time | Comparison preparation (EXAMPLE A) | Preparation according to invention (EXAMPLE 1) |
| 5 min | 3.67 | 4.37 |
| 10 min | 5.25 | 6.10 |
| 15 min | 6.05 | 6.84 |
| 20 min | 6.32 | 7.13 |
| 30 min | 6.71 | 7.41 |
| 40 min | 6.78 | 7.51 |
| 60 min | 6.97 | 7.70 |

N.B. The reported values are the mean of at least three repeats; average C.V. 5–7%

TABLE 2

Dissolution rate of products consisting of griseofulvin/crospovidone 1:1 weight/weight

| Time | Griseofulvin concentration (μg/ml) | |
|---|---|---|
| | Comparison preparation (EXAMPLE B) | Preparation according to invention (EXAMPLE 2) |
| 5 min | 2.90 | 3.05 |
| 10 min | 3.75 | 4.32 |
| 15 min | 4.40 | 5.10 |
| 20 min | 4.85 | 5.50 |
| 30 min | 5.23 | 5.82 |
| 40 min | 5.45 | 6.15 |

N.B. The reported values are the mean of at least three repeats; maximum C.V. 5–6%

TABLE 3

Dissolution rate of products consisting of diacerein/crospovidone 1:3 weight/weight

| Time | Diacerein concentration (μg/ml) | |
|---|---|---|
| | Comparison preparation (EXAMPLE C) | Preparation according to invention (EXAMPLE 3) |
| 1 min | 9.78 | 11.89 |
| 3 min | 13.64 | 19.83 |
| 5 min | 15.27 | 23.02 |
| 10 min | 17.08 | 24.51 |
| 15 min | 18.26 | 25.45 |
| 30 min | 19.47 | 26.01 |
| 45 min | 21.95 | 25.17 |
| 60 min | 23.01 | 26.70 |

N.B. The reported values are the mean of at least three repeats; average C.V. 6%

TABLE 4

Dissolution rate of products consisting of megestrol acetate/crospovidone 1:3 weight/weight

| Time | Megestrol acetate concentration (μg/ml) | |
|---|---|---|
| | Comparison preparation (EXAMPLE E) | Preparation according to invention (EXAMPLE 5) |
| 5 min | 0.143 | 0.150 |
| 10 min | 0.262 | 0.306 |
| 20 min | 0.354 | 0.382 |
| 30 min | 0.387 | 0.418 |
| 45 min | 0.401 | 0.454 |
| 60 min | 0.405 | 0.462 |
| 90 min | 0.401 | 0.462 |
| 120 min | 0.413 | 0.465 |

N.B. The reported values are the mean of at least three repeats; average C.V. 6%

TABLE 5

Dissolution rate of products consisting of piroxicam/crospovidone 1:3 weight/weight

| Time | Piroxicam concentration (μg/ml) | |
|---|---|---|
| | Comparison preparation (EXAMPLE F) | Preparation according to invention (EXAMPLE 6) |
| 5 min | 1.11 | 2.09 |
| 10 min | 1.77 | 2.70 |
| 15 min | 2.23 | 2.88 |
| 20 min | 2.53 | 3.01 |
| 30 min | 2.61 | 3.03 |
| 40 min | 2.72 | 3.03 |
| 60 min | 2.72 | 3.24 |

N.B. The reported values are the mean of at least three repeats; average C.V. 6%

TABLE 6

Dissolution rate of products consisting of megestrol acetate/β-cyclodextrin 1:3 weight/weight

| Time | Megestrol acetate concentration (μg/ml) | |
|---|---|---|
| | Comparison preparation (EXAMPLE G) | Preparation according to invention (EXAMPLE 7) |
| 5 min | 0.017 | 0.033 |
| 10 min | 0.028 | 0.056 |
| 20 min | 0.048 | 0.108 |

TABLE 6-continued

Dissolution rate of products consisting of megestrol acetate/β-cyclodextrin 1:3 weight/weight

| Time | Megestrol acetate concentration (μg/ml) | |
|---|---|---|
| | Comparison preparation (EXAMPLE G) | Preparation according to invention (EXAMPLE 7) |
| 30 min | 0.0961 | 0.135 |
| 45 min | 0.121 | 0.168 |
| 60 min | 0.151 | 0.199 |
| 90 min | 0.187 | 0.240 |
| 120 min | 0.208 | 0.272 |

N.B. The reported values are the mean of at least three repeats; average C.V. 9%

TABLE 7

Dissolution rate of products consisting of piroxicam/β-cyclodextrin 1:3 weight/weight

| Time | Piroxicam concentration (μg/ml) | |
|---|---|---|
| | Comparison preparation (EXAMPLE I) | Preparation according to invention (EXAMPLE 9) |
| 10 min | 0.100 | 2.15 |
| 15 min | 0.107 | 2.73 |
| 20 min | 0.134 | 3.28 |
| 30 min | 0.150 | 3.34 |
| 40 min | 0.157 | 3.49 |
| 60 min | 0.165 | 3.59 |
| 120 min | 0.169 | 3.68 |

N.B. The reported values are the mean of at least two-three repeats; average C.V. 6%

TABLE 8

Dissolution rate of products consisting of griseofulvin/cross-linked β-cyclodextrin 1:3 weight/weight

| Time | Griseofulvin concentration (μg/ml) | |
|---|---|---|
| | Comparison preparation (EXAMPLE M) | Preparation according to invention (EXAMPLE 11) |
| 5 min | 1.00 | 1.82 |
| 10 min | 1.78 | 2.46 |
| 15 min | 2.57 | 2.98 |
| 20 min | 2.69 | 3.48 |
| 30 min | 3.34 | 4.01 |
| 60 min | 4.26 | 4.41 |

N.B. The reported values are the mean of two repeats; average C.V. 2–3%

TABLE 9

Dissolution rate of products consisting of piroxicam/silica gel 1:3 weight/weight

| Time | Piroxicam concentration (μg/ml) | |
|---|---|---|
| | Comparison preparation (EXAMPLE N) | Preparation according to invention (EXAMPLE 12) |
| 5 min | 0.44 | 0.81 |
| 10 min | 0.80 | 1.37 |
| 15 min | 1.08 | 1.62 |
| 20 min | 1.27 | 1.74 |
| 30 min | 1.48 | 1.97 |
| 40 min | 1.60 | 2.09 |
| 60 min | 1.80 | 2.30 |
| 120 min | 2.04 | 2.78 |

N.B. The reported values are the mean of two repeats; average C.V. 5–7%

Determination of solubilization kinetics

The solubilization kinetics tests were conducted under non-sink conditions (i.e. with the drug in excess over its solubility). For all the studied products the method used was the following: the co-ground product is placed in flasks with 40–50 ml of preheated buffer solution at the chosen pH; the flasks are placed in a CELLAI cupboard temperature-controlled at 37° C. and stiffed (100–150 r.p.m.). At predetermined times an aliquot of the solution is withdrawn and filtered; the solution is then analyzed using a BECKMAN DU 65 spectrophotometer. For products containing megestrol acetate 75 mg of product were used in 50 ml of buffer solution at pH 5.5, the spectrophotometric reading being taken at 296 nm with 4 cm cells. Stirring was at 150 p.p.m. For products containing piroxicam 1.04 g of product were used in 40 ml of buffer solution at pH 5.0, with stirring at 100 r.p.m.. The spectrophotometric reading was taken at 356 nm. As can be seen from the data shown in Tables 10 and 11, in all cases there was a higher solubilization kinetics for the products prepared by the processes of the present invention compared with analogous products prepared by the known art.

TABLE 10

Solubilization kinetics of products consisting of megestrol acetate/crospovidone 1:2 weight/weight Megestrol acetate concentration (μg/ml)

| Time | Comparison preparation (EXAMPLE D) | Preparation according to invention (EXAMPLE 4) |
|---|---|---|
| 15 sec | 5.76 | 6.96 |
| 30 sec | 7.73 | 12.96 |
| 45 sec | 8.80 | 11.19 |
| 1 min | 9.01 | 16.21 |
| 3 min | 9.95 | 19.50 |
| 5 min | 11.71 | 16.38 |
| 15 min | 11.74 | 22.19 |
| 1 hr | 11.01 | 25.84 |

TABLE 11

Solubilization kinetics of products consisting of prixicam-β-cyclodextrin 1:9.16 weight/weight Piroxicam concentration (μg/ml)

| Time | Comparison preparation (EXAMPLE H) | Preparation according to invention (EXAMPLE 8) |
|---|---|---|
| 30 sec | 99.8 | 200.5 |
| 1 min | 142.8 | 198.5 |
| 2 min | 148.4 | 248.4 |
| 5 min | 165.6 | 292.9 |
| 10 min | 157.7 | 266.5 |
| 15 min | 132.1 | 251.4 |
| 30 min | 97.8 | 239.6 |
| 60 min | 99.5 | 211.0 |

Differential scanning calorimeter data

A further characteristic of the products prepared by the process of this invention is that they have a high energy crystalline state characterised by a lower melting point than the drug as such and a lower heat of fusion.

The melting point depression is related to the formation of very fine crystals, in the nanometer dimensional range, and known as "nanocrystals" (F. carli et al., Proceedings of 13th Controlled Release Bioactive Materials Symposium, Norfolk, USA, 1986; Proceedings of Ind. Pharm. Techn. Conf., London 1988).

Table 12 shows the thermoanalytical data relative to products prepared in accordance with the invention, obtained using a TA 3000 differential scanning calorimeter of Mettler (Switzerland), with nitrogen flow and a heating rate of 10° K. min $^{-1}$. The same table also shows data relative to products prepared by the known co-grinding method, and data relative to the crystalline active principles as such. As can be seen, in all cases the products prepared in accordance with this invention have melting peaks at much lower temperatures than products prepared by known methods.

TABLE 12

Differential scanning calorimetry data for products prepared by the method of the invention and by the traditional method

| | THERMAL CHARACTERISTICS | MELTING POINT | HEAT OF FUSION |
|---|---|---|---|
| Griseofulvin as such: | only 1 peak | 219.8° C. | 120.4 J/g |
| Griseofulvin/crospovidone 1:2 weight/weight: | | | |
| Example A[a] | only 1 peak | 203.4° C. | 57.4 J/g |
| Example 1[b] | 2 peaks | 204.1° C. | 25.8 J/g |
| | | 190.0° C. | 38.7 J/g |
| Megestrol acetate as such: | only 1 peak | 217.5° C. | 83.5 J/g |
| Megestrol acetate/crospovidone 1:2 weight/weight: | | | |
| Example D[a] | only 1 peak | 205.2° C. | 34.7 J/g |
| Example 4[b] | only 1 peak | 193.1° C. | 36.9 J/g |
| Megestrol acetate/β-cyclodextrin 1:3 weight/weight: | | | |
| Example G[a] | only 1 peak | 218.7° C. | 83.4 J/g |
| Example 7[b] | only 1 peak | 215.6° C. | 82.7 J/g |

[a]products prepared by traditional method
[b]products prepared in accordance with this invention

I claim:

1. A process for the preparation of a drug on a support material wherein which comprises the steps of:
   (a) mixing a drug and a support material in the form of powders to form a mixture;
   (b) grinding said mixture in a grinding chamber which is saturated with the vapor of a solvent which is adsorbed on the surface of said support material to form a ground mixture;
   (c) drying said ground mixture under vacuum; and
   (d) sieving said ground mixture to eliminate any aggregates formed.

2. The process as claimed in claim 1, wherein said drug is an anti-flammatory, an analgesic, a tranquilizer, a sedative or an antitumor agent.

3. The process as claimed in claim 1, wherein said drug is selected from the group consisting of griseofulvin, piroxicam, diacerein, diltiazem, megestrol acetate, nifedipine, nicergoline, ketoprofen, naproxen, diclofenac, ibuprofen, lorazepan and oxazepam.

4. The process as claimed in claim 1, wherein said support material is a cross-linked polymer swellable in water.

5. A process as claimed in claim 1, wherein the weight ratio of said support material to said drug is between 100:1 and 1:10.

6. A process as claimed in claim 1, wherein the weight ratio of said support material to said drug is between 10:1 to 1:1.

7. A process as claimed in claim 1, wherein said solvent is selected from the group consisting of water, methylenechloride, chloroform, methanol, ethanol, isopropanol and a mixture thereof.

8. A process as claimed in claim 1, wherein said grinding chamber selected from the group consisting of a rotary mill, a ball mill, a roller mill, a mortar mill and a planetary mill.

9. A process as claimed in claim 1, wherein said co-grinding is conducted for a time of between 0.10 and 48 hours.

10. The process according to claim 1 further comprising subjecting said mixture of step (a) to degassing.

11. The process according to claim 1 wherein said active substance is piroxicam; and said support material is crospovidone.

12. A process for preparing a drug on a support which comprises the steps of a) mixing said drug and support material, which is a polymer swellable in water each in the form of a powder; b) grinding said mixture in a mill having a grinding chamber wherein said grinding chamber is saturated with a solvent which is adsorbed on the surface of said support material to form a ground mixture; c) drying said ground mixture under vacuum; and (d) sieving said ground mixture through a 60 mesh sieve to eliminate any aggregates formed.

13. A process for the preparation of a drug in a cross-linked polymer support material, which comprises the steps of:
  (a) mixing a drug and a cross-linked polymer support material to form a mixture said drug and said cross-linked polymer support being in powder form;
  (b) grinding said mixture in a grinding chamber in the presence of a saturated vapor of a solvent which is adsorbed on the surface of said support material for a period of 0.25 to 4.0 hours to form a ground mixture;
  (c) drying said ground mixture under vacuum; and
  (d) sieving said ground mixture to eliminate any aggregates formed.

14. The process according to claim 1 wherein said support material is selected from the group consisting of crospovidone, cross-linked sodium carboxymethyl starch, cyclodextrin, silica gel and aluminum oxides.

* * * * *